(12) United States Patent
    Kawabata

(10) Patent No.: US 10,433,758 B2
(45) Date of Patent: Oct. 8, 2019

(54) BIOLOGICAL INFORMATION MEASURING APPARATUS

(71) Applicant: National University Corporation Tokyo Medical and Dental University, Tokyo (JP)

(72) Inventor: Shigenori Kawabata, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 102 days.

(21) Appl. No.: 15/570,509

(22) PCT Filed: Apr. 11, 2016

(86) PCT No.: PCT/JP2016/061734
    § 371 (c)(1),
    (2) Date: Oct. 30, 2017

(87) PCT Pub. No.: WO2016/175020
    PCT Pub. Date: Nov. 3, 2016

(65) Prior Publication Data
    US 2018/0140215 A1    May 24, 2018

(30) Foreign Application Priority Data

Apr. 30, 2015 (JP) ................. 2015-092892

(51) Int. Cl.
    *A61B 5/05*      (2006.01)
    *A61B 6/00*      (2006.01)
    (Continued)

(52) U.S. Cl.
    CPC ............ *A61B 5/05* (2013.01); *A61B 5/04005* (2013.01); *A61B 6/00* (2013.01);
    (Continued)

(58) Field of Classification Search
    None
    See application file for complete search history.

(56) References Cited

U.S. PATENT DOCUMENTS 5,794,620 A    8/1998  Dossel et al.
6,522,908 B1   2/2003  Miyashita et al.
               (Continued)

FOREIGN PATENT DOCUMENTS

JP    H02-249530 A    10/1990
JP    H05-184552 A    7/1993
                     (Continued)

OTHER PUBLICATIONS

Office Action issued in counterpart European Patent Application No. 16786297.8, dated May 25, 2018 (6 Pages).
(Continued)

*Primary Examiner* — Edwin C Gunberg
(74) *Attorney, Agent, or Firm* — Osha Liang LLP

(57) ABSTRACT

A biological information measuring apparatus includes a radiation emitting unit configured to emit radiation to a subject, a biomagnetic field detector configured to detect a biomagnetic field on the subject, and a radiation sensitive material having sensitivity to the radiation, having enough size for enabling radiography of an examination target of the subject, and being nonmagnetic. The radiation sensitive material is arranged between an examination region where the examination target of the subject is to be positioned and the biomagnetic field detector.

19 Claims, 9 Drawing Sheets

(51) Int. Cl.
*A61B 5/04* (2006.01)
*A61B 90/00* (2016.01)

(52) U.S. Cl.
CPC ............... *A61B 2090/3958* (2016.02); *A61B 2562/0223* (2013.01); *A61B 2562/164* (2013.01)

(56) References Cited

U.S. PATENT DOCUMENTS

| | | |
|---|---|---|
| 6,628,978 B1 | 9/2003 | Kondo et al. |
| 8,583,208 B2 | 11/2013 | Adachi et al. |
| 2009/0012384 A1 | 1/2009 | Adachi et al. |

FOREIGN PATENT DOCUMENTS

| | | |
|---|---|---|
| JP | 2001-037761 A | 2/2001 |
| WO | 99/49781 A1 | 10/1999 |
| WO | 2006/122278 A2 | 11/2006 |
| WO | 2007/099697 A1 | 9/2007 |
| WO | 2008/127720 A2 | 10/2008 |

OTHER PUBLICATIONS

Supplementary European Search Report issued in counterpart European Patent Application No. 16786297.8, dated May 4, 2018 (4 Pages).
International Search Report of the International Searching Authority issued in PCT/JP2016/061734 dated Jul. 12, 2016 (1 page).
Written Opinion of the International Searching Authority issued in PCT/JP2016/061734 dated Jul. 12, 2016 (3 pages).

CHEST RADIOGRAPHIC IMAGE

CERVICAL-VERTEBRAE RADIOGRAPHIC IMAGE

LUMBAR-VERTEBRAE RADIOGRAPHIC IMAGE

MAGNETOCARDIOGRAM WHEN THE IMAGING PLATE IS ARRANGED OVER BIOMAGNETISM DETECTING SURFACE

BIOLOGICAL INFORMATION MEASURING APPARATUS

TECHNICAL FIELD

The present invention relates to a biological information measuring apparatus.

BACKGROUND ART

A biomagnetic field measurement apparatus, with which weak biomagnetic field arising from the heart, spinal cord, peripheral nerve, and the like of a subject can be measured, has a function of detecting magnetic field due to a weak current generated upon stimulating cells constituting these organs. Correlating measurement results from a biomagnetic field measurement apparatus with morphological positions of an organ as measurement target is important technology for diagnosing cardiac diseases, spinal diseases, peripheral nerve diseases, and the like. Accordingly, a technology has been proposed in which marker coils are attached on a plurality of locations of a subject, and a morphological image is acquired with a diagnostic imaging apparatus (an X-ray emitting device, CT, MRI, and the like) at a place different from that of a biomagnetic field measurement apparatus, and results obtained from the biomagnetic field measurement apparatus are superimposed over the morphological image from the diagnostic imaging apparatus (for example, see Patent Document 1).

The precise correspondence between the results obtained from a biomagnetic field measurement apparatus and a morphological image from a diagnostic imaging apparatus (for example, an X-ray emitting device) is required in order to more precisely reflect the measuring results from the biomagnetic field measurement apparatus. However, when a subject is transferred between an X-ray emitting device and a biomagnetic field measurement apparatus, the truncus (spinal cord) of the subject may be bent or warped in the anterior-posterior direction and/or the right-left direction, or the limb joints of the subject may be bent or stretched. Therefore, the precise correspondence between the positional information about the subject at the X-ray emitting device and the positions of the subject upon examination with the biomagnetic field measurement apparatus is very difficult.

In order to increase the correspondence precision, it has been proposed that data sets from an imaging means and a SQUID are processed with a biomagnetic field measurement apparatus including both of the imaging means and the SQUID, the imaging means being configured to capture tomogram of a living body, and the SQUID being configured to measure a magnetic field arising from a marker coil (for example, see Patent Documents 2 and 3).

Patent Document 1: PCT International Publication No. WO99/49781
Patent Document 2: Japanese Unexamined Patent Application, Publication No. H05-184552
Patent Document 3: PCT International Publication No. WO2007/099697

DISCLOSURE OF THE INVENTION

Problems to be Solved by the Invention

However, depending on the positional relationship between a biomagnetic field measurement apparatus and an X-ray emitting device, the biomagnetic field measurement apparatus may be projected to block a subject when the subject is imaged with the X-ray emitting device. This may prevent the subject from being imaged. Moreover, a cartridge in which a radiation-sensitive material is contained is magnetized, and the magnetism from the cartridge may have a negative impact on measuring results from a biomagnetic field measurement apparatus depending on the positional relationship between the biomagnetic field measurement apparatus and an X-ray emitting device. Therefore, even according to the approaches of Patent Documents 2 and 3, the measuring results from a biomagnetic field measurement apparatus and the morphological image from an X-ray emitting device may not be obtained in high precision for all the organs of a subject.

The present invention is made in view of solving the above problems. An object of the present invention is to simply and precisely achieve both morphological image measurements of a subject with a diagnostic imaging apparatus such as an X-ray emitting device and detection of biomagnetic field with a biomagnetic field measurement apparatus without changing the position of the subject such that the projection of the biomagnetic field measurement apparatus is prevented which may occur when imaging the subject with the diagnostic imaging apparatus, and a negative impact of the magnetism of a cartridge on the biomagnetic field measurement apparatus is reduced.

Means for Solving the Problems

The present inventors have conducted extensive studies in order to achieve the above object. As a result, the present investors found that the above object can be achieved by preparing a radiation sensitive material having sensitivity to radiation such as X rays and having a size enough for enabling radiography of an examination target of a subject and being nonmagnetic; and arranging the radiation sensitive material between an examination region where the examination target of the subject is to be positioned and a biomagnetic field detector. Then the present invention has been completed. Specifically, the present invention provides the followings.

(1) An embodiment of the present invention is a biological information measuring apparatus including: a radiation emitting unit configured to emit radiation to a subject; a biomagnetic field detector configured to detect biomagnetic field of the subject; and a radiation sensitive material having sensitivity to the radiation and having a size enough for enabling radiography of an examination target of the subject and being nonmagnetic, the radiation sensitive material being arranged between an examination region where the examination target of the subject is to be positioned and the biomagnetic field detector.

(2) Further, another embodiment of the present invention is the biological information measuring apparatus according to (1), in which the biomagnetic field detector includes: a magnetic sensor configured to detect the biomagnetic field of the subject; and a sensor container configured to contain the magnetic sensor, the sensor container having a biomagnetic field detecting surface, the biomagnetic field detecting surface facing to the examination region where the examination target of the subject is to be positioned, the radiation sensitive material being arranged over the biomagnetic field detecting surface.

(3) Further, another embodiment of the present invention is the biological information measuring apparatus according to (1) or (2), in which the radiation sensitive material is flexible.

(4) Further, another embodiment of the present invention is the biological information measuring apparatus according to any one of (1) to (3), in which the radiation sensitive material is stored in a state where the radiation sensitive material is enclosed in a storage member, the storage member being nontransmissible of visible light and being nonmagnetic.

(5) Further, another embodiment of the present invention is the biological information measuring apparatus according to any one of (1) to (4), in which a magnetic marker configured to generate a predetermined magnetic field is arranged at a surface side of the radiation sensitive material.

(6) Further, another embodiment of the present invention is the biological information measuring apparatus according to any one of (1) to (4), further including a nonmagnetic member covering the radiation sensitive material, a position of the nonmagnetic member relative to the biomagnetic field detector being fixed, a radiation nontransmissible and nonmagnetic marker being arranged at a surface of the nonmagnetic member opposite to a side of the biomagnetic field detector.

(7) Further, another embodiment of the present invention is the biological information measuring apparatus according to any one of (1) to (4), further including a nonmagnetic member covering the radiation sensitive material and fixed at a position relative to the biomagnetic field detector; and a positioning mechanism configured to specifying the position of the radiation sensitive material relative to the nonmagnetic member.

Effects of the Invention

An embodiment of the present invention includes a radiation sensitive material having sensitivity to radiation, and having a size enough for enabling radiography of an examination target of a subject, and being nonmagnetic. Therefore, a radiological image of a subject can be captured by emitting radiation to the subject, and exposing an irradiation state to the radiation sensitive material. At that time, the biomagnetic field detector is located in the back side of the radiation sensitive material viewed from the irradiation direction of the radiation from the radiation emitting unit, avoiding the projection of the biomagnetic field detector into the radiological image.

In general, a radiation sensitive material is enclosed in a cartridge, and in a magnetized state. The magnetism arising from a subject is very weak. Therefore, a magnetized radiation sensitive material arranged between a radiation emitting unit and a biomagnetic field detector may have a negative impact on detection results from the biomagnetic field detector.

In contrast, according to the present invention, the radiation sensitive material is nonmagnetic, and thus the magnetism from a subject can suitably be detected without removing the radiation sensitive material from the biological information measuring apparatus even when detecting the magnetism from the subject at the biomagnetic field detector. Advantageous effects of the present invention are as follows: the projection of a biomagnetic field detector into a radiological image can be avoided; and further, both radiological image measurements and biomagnetic field detection of a subject can be simply and precisely achieved without changing the position of the subject such that the radiation sensitive material does not have a negative impact on the biomagnetic field detection.

PREFERRED MODE FOR CARRYING OUT THE INVENTION

Below, specific embodiments of the present invention will be described in detail. A first embodiment represents an example in which a subject lies on a bed, and both a radiological image measurement of the chest of a subject and a magnetocardiographic examination of the subject are performed without changing the position of the subject. A second embodiment differs from the first embodiment in that the subject is located in the standing position. A third embodiment differs from the first embodiment in that an examination target of the subject is the spinal cord/spinal nerve or a magnetocardiogram of the posterior side. Examinations according to the first and third embodiments in which the bed is used are intended for in-hospital thorough examinations. Examinations in the standing position according to the second embodiment are intended for simple examinations where chest plain radiography and magnetocardiography are performed simultaneously in an examination room, an examination car, and the like.

The present invention is not limited to the first to third embodiments in any sense, and can be implemented with appropriate modifications made within the scope of the present invention. It is noted that description for repeatedly appearing parts may be omitted if appropriate, but this shall not limit the spirit of the present invention.

First Embodiment

First, the first embodiment of the present invention is described.

[Biological Information Measuring Apparatus 1]

Figure 1:
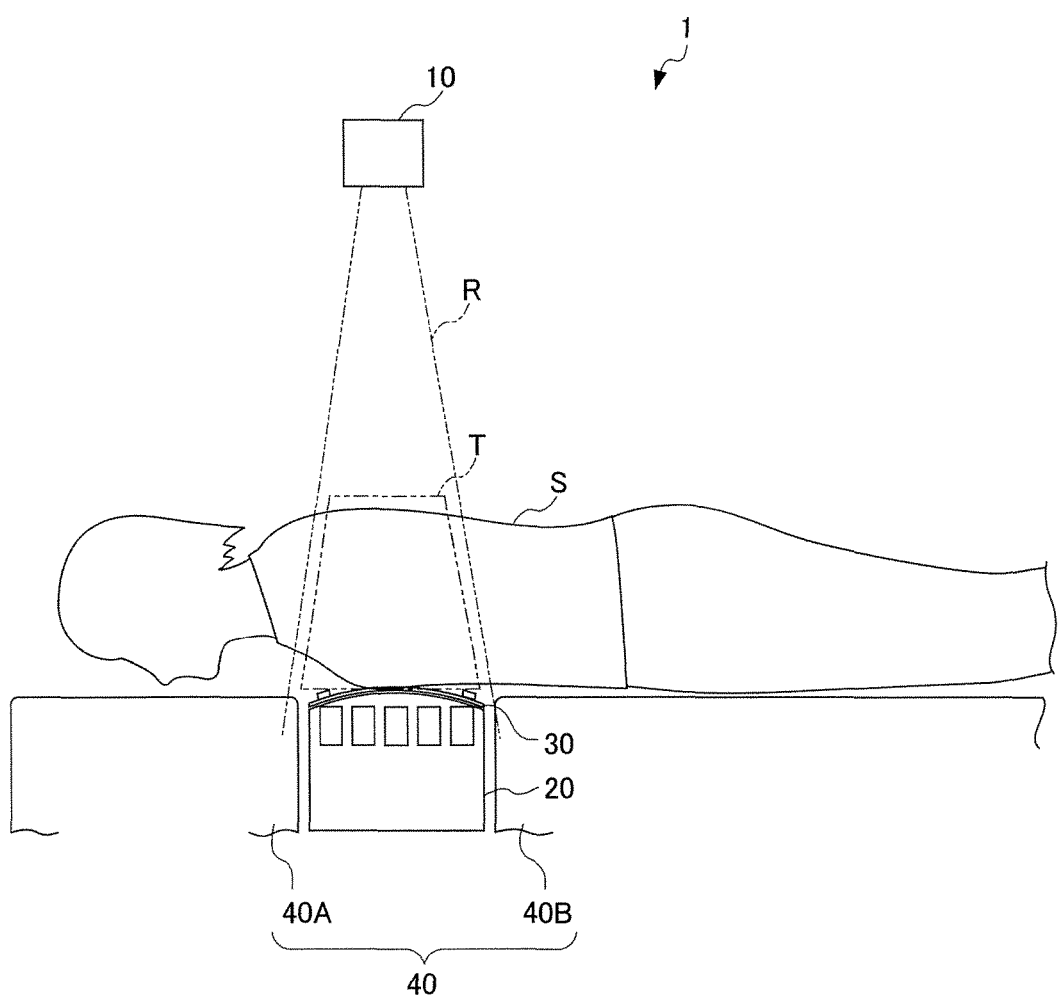
FIG. 1 shows a schematic view of a biological information measuring apparatus 1 according to a first embodiment of the present invention.

FIG. 1 shows a schematic view of the biological information measuring apparatus 1 according to the present invention. The biological information measuring apparatus 1 includes a radiation emitting unit 10 configured to emit radiation R to a subject S, a biomagnetic field detector 20 configured to detect biomagnetic field of the subject S, and a radiation sensitive material 30 having sensitivity to radiation and having a size enough for enabling radiography of an examination target of the subject S and being nonmagnetic. The biological information measuring apparatus 1 further includes a bed 40 on which the subject S is to be positioned, the bed 40 including a head-supporting bed 40A on which the head of the subject S is to be positioned and a leg-supporting bed 40B on which the legs of the subject S is to be positioned. The biomagnetic field detector 20 is arranged between the head-supporting bed 40A and the leg-supporting bed 40B, and provided so as to face an examination region T where the examination target of the subject S is to be positioned. Further, the radiation sensitive material 30 is arranged between the examination region T where the examination target of the subject S is to be positioned and the biomagnetic field detector 20.

The first embodiment is described with reference to a case where the subject S is positioned in the prone position (in the abdominal position) on the bed 40, and the examination target of the subject S for a radiographic examination is the chest, and the examination target of the subject S for biomagnetic field detection is the heart. But the first embodiment shall not be limited to this.

[Radiation Emitting Unit 10]

The radiation emitting units 10 may be in any known configuration, and may be an X-ray emitting device configured to emit X-rays, or an α-ray emitting device configured to emit α-rays, a β-ray emitting device configured to emit β-rays, a γ-ray irradiation device configured to emit γ-rays, and the like.

[Biomagnetic Field Detector 20]

Figure 2:
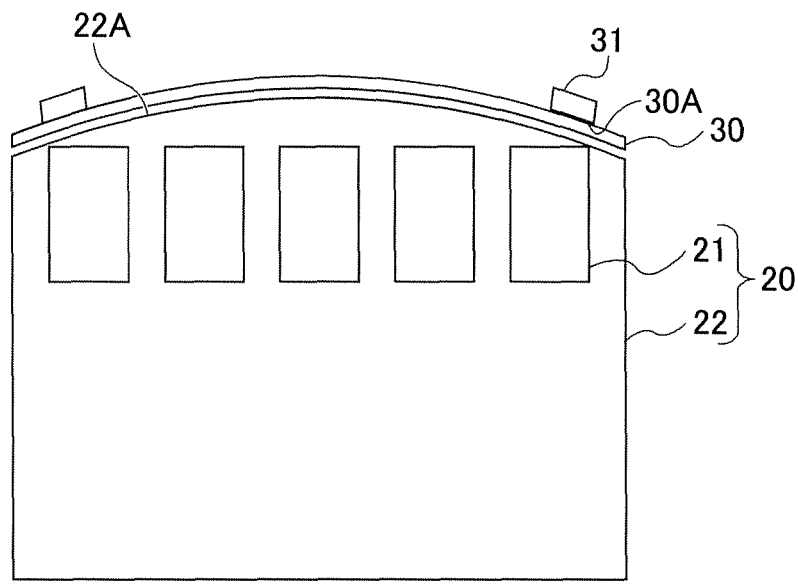
FIG. 2 shows an example of a biomagnetic field detector 20 and a radiation sensitive material 30 constituting the biological information measuring device 1.

FIG. 2 represents an example of the biomagnetic field detector 20 and the radiation sensitive material 30 constituting the biological information measuring apparatus 1. The biomagnetic field detector 20 includes a magnetic sensor 21 configured to detect the biomagnetic field of the subject S.

Specific configurations of the biomagnetic field detector 20 include an SQUID (Superconducting QUantum Interference Device) device, a magnetoresistivity element (MR (AMR, GMR, TMR, and the like)), a magnetoimpedance element (MI element), a flux-gate sensor, a hall element, an optical pumping atomic magnetic sensor, and the like. When the biomagnetic field detector 20 is an SQUID device, an SQUID sensor corresponds to the magnetic sensor 21.

Usually, a plurality of the magnetic sensors 21 are provided. When the biomagnetic field detector 20 is an SQUID device, the magnetic sensor 21 is fixed in the inside of a sensor container 22 configured to create the superconductive state. It is noted that sensors other than the SQUID sensor need not be placed in the container, and for example, the position of each sensor may be changed so as to make close contact with the subject.

The sensor container 22 is also referred to as a cryostat, and has a biomagnetic field detecting surface 22A facing the examination region T where the examination target of the subject S is to be positioned. The sensor container 22 is preferably a vacuum insulated container, and configured to be filled with liquid helium in the inside to maintain the magnetic sensor 21 at low temperature for achieving the superconductive state.

There is no particular limitation for the shape of the sensor container 22, but the biomagnetic field detecting surface 22A preferably has a shape according to the body surface of the examination target of the subject S so as to be parallel with the body surface of the examination target of the subject S. For example, when operating the biomagnetic field detector 20 as a magnetocardiography meter as in the first embodiment, the biomagnetic field detecting surface 22A may have a planer shape or a gradually convex wave-like shape. Meanwhile, when operating the biomagnetic field detector 20 as a spinal magnetometer, the biomagnetic field detecting surface 22A preferably has a gradually convex wave-like shape.

The sensor container 22 is preferably placed inside a magnetic-shielding dome (not shown) made of an electromagnetic-wave blocking material such as permalloy and aluminum in order to block electromagnetic waves other than biomagnetic field, reducing a negative impact of electromagnetic waves on the magnetic sensor 21.

[Radiation Sensitive Material 30]

The radiation sensitive material 30 is arranged between the examination region T where the examination target of the subject S is to be positioned and the biomagnetic field detector 20. Specifically, the radiation sensitive material 30 is preferably arranged over the biomagnetic field detecting surface 22A. When the radiation sensitive material 30 is arranged at an inappropriate position, both of the radiological image measurement and biomagnetic field detection of a subject cannot be performed without changing the position of the subject S. In particular, it is difficult to correlate measuring results from the biomagnetic field detector 20 with morphological positions of an organ as a measurement target. Therefore, that configuration is not preferred.

The radiation sensitive material 30 is sensitive to the radiation R. A radiation sensitive material 30 insensitive to radiation is not preferred in that a radiographic image of the examination target of the subject S cannot be suitably obtained even when the subject S is irradiated with the radiation R from the radiation emitting unit 10.

The radiation as used herein is not limited to commonly used X-rays, and encompasses a comprehensive concept including α-, β-, and γ-rays, and the like as a beam of particles (including photons) emitted upon radioactive decay, a beam having an energy equal to or more than those beams above, for example, particle beams, cosmic rays, and the like. X-rays are preferably used as radiation in view of their high versatility.

Further, the radiation sensitive material 30 is nonmagnetic. A radiation sensitive material 30 having magnetism is not preferred in that the magnetism arising from the radiation sensitive material 30 may have a negative impact on the detection precision of the biomagnetic field detector 20.

By the way, the radiation sensitive material 30 is typically used in a state where it is enclosed in a cartridge in accordance with International Standard ISO4090:2001. This is because when the radiation sensitive material 30 generally and widely used, which is sensitive to not only the radiation R but also visible light, is left in an exposure state (in a state where it is not enclosed in the cartridge), the radiation sensitive material 30 may undergo discoloration due to visible light. This may have a negative impact on the precision of a radiography examination. However, the cartridge includes a magnetic material, and thus magnetism is generated not only from the subject S but also from the cartridge of the radiation sensitive material 30 when the radiation sensitive material 30 is enclosed in the cartridge in the present invention. This may have a negative impact on detection results from the biomagnetic field detector 20. Therefore, in the present invention, the radiation sensitive material 30 is clearly distinguished from that in a state where it is enclosed in the cartridge.

The radiation sensitive material 30 is sized enough for enabling radiography of the examination target of the subject S. A too small radiation sensitive material 30 is not preferred in that the examination target of the subject S cannot be suitably radiographed.

The radiation sensitive material 30 is preferably flexible. When the radiation sensitive material 30 is flexible, the shape of the radiation sensitive material 30 can be changed according to the shape of the biomagnetic field detecting surface 22A regardless of the shape of the biomagnetic field detecting surface 22A.

Specific examples of the radiation sensitive material 30 include radiography films, imaging plates, and the like. The term "imaging plate" refers to a sensitive material in which an image obtained upon radiation exposure can be digitally recorded. Imaging plates are widely used in recent years because they are reusable unlike radiography films.

The conventional radiography film and imaging plate are sensitive to not only the radiation R but also visible light. Therefore, when the conventional radiography film and imaging plate are left in an exposure state (in a state where they are not enclosed in cartridges), the radiography film and imaging plate may undergo discoloration due to visible light. This may have a negative impact on the precision of a radiography examination. Accordingly, the radiation sensitive material 30 is preferably stored in a state where it is enclosed in a storage member which is non-transmissible of visible light. Preferably, the storage member is opened to bring the radiation sensitive material 30 into an exposure state immediately before biological information is measured with the biological information measuring apparatus 1 according to the present invention.

The storage member is preferably nonmagnetic in contrast to the cartridge. Specifically, when the radiation sensitive material 30 is enclosed in a storage member which is nonmagnetic and made of a material allowing radiation to transmit but not allowing visible light to transmit (for example, light-blocking paper, plastics, vinyl, and the like), radiological image measurements and biomagnetic field detection can be performed while it remains enclosed. Further, the radiation sensitive material 30 is not exposed to visible light at all. This can increase the precision of radiological image measurements. Further, the storage member is nonmagnetic, and thus the precision of biomagnetic field detection is not decreased. It is noted that the storage member is preferably thin enough not to increase the distance between the subject S and the biomagnetic field detecting surface 22A. Moreover, the storage member is preferably flexible as the radiation sensitive material 30.

Alternatively, the radiation sensitive material 30 itself preferably does not transmit visible light. When the radiation sensitive material 30 itself is configured to be non-sensitive to visible light, discoloration of the radiation sensitive material 30 can be prevented without enclosing the radiation sensitive material 30 in the storage member for storage.

Although not an essential component, a magnetic marker 31 configured to generate a predetermined magnetic field is preferably provided on a surface 30A of the radiation sensitive material 30 to increase the precision of correlating detection results from the biomagnetic field detector 20 to morphological positions of an organ as the measurement target by overlaying the detection results from the biomagnetic field detector 20 over a radiological image (a morphological image of the measurement target) obtained using the radiation emitting unit 10 and the radiation sensitive material 30. Here, the magnetic marker 31 is arranged within the detection range of the biomagnetic field detector 20 so that the acquisition of positional information of the subject S using the radiation R is not interfered (for example, at a peripheral portion of the biomagnetic field detecting surface 22A, and the like). It is noted that the magnetic marker 31 is provided on a surface of a storage member when the radiation sensitive material 30 is enclosed in the storage member.

Any conventionally known types of magnetic markers can be used as the magnetic marker 31. Examples include a small coil adhesive-sheet called a marker coil. The marker coil is energized to generate a weak magnetic field, which is detected by the magnetic sensor 21. Then a position where the magnetic field has been generated by the marker coil is computed in a position computing unit (not shown) of the biomagnetic field detector 20. That position can be used as a reference when detection results from the biomagnetic field detector 20 are superimposed over a radiological image.

There is no particular limitation for the number of magnetic markers, as long as it is more than one. The number of magnetic markers is preferably larger in order to increase the precision of determining the shape of a measurement target. The number of magnetic markers is preferably smaller in order to reduce noise from magnetic markers to precisely detect the magnetism from a subject with the biomagnetic field detector. Considering the both, the number of magnetic markers is preferably 2 or more and 6 or less, more preferably 2 or more and 4 or less.

Figure 3:
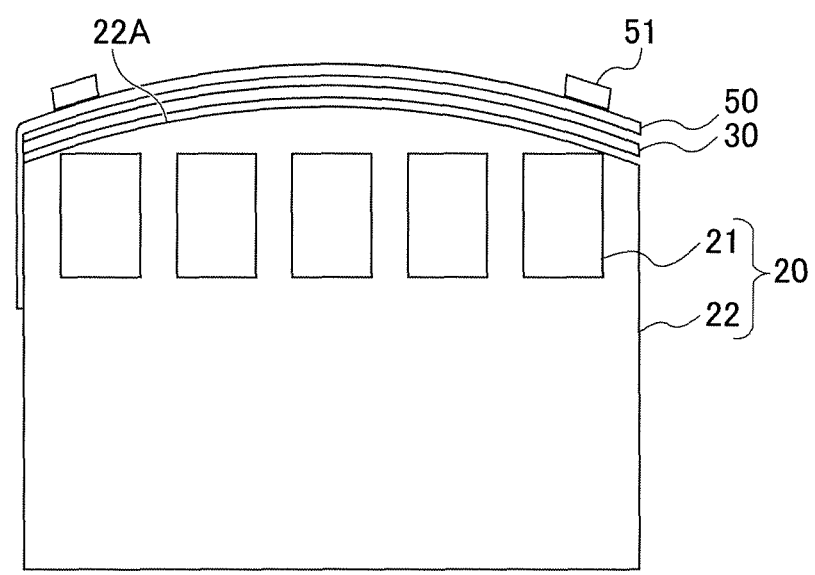
FIG. 3 shows another example of the biomagnetic field detector 20 and the radiation sensitive material 30 constituting the biological information measuring device 1.

As another example in which the precision of correlating detection results from the biomagnetic field detector 20 to morphological positions of an organ as a measurement target, an configuration shown in FIG. 3 can be mentioned. In FIG. 3, a nonmagnetic member 50 covering the radiation sensitive material 30 is provided. The nonmagnetic member 50 is attached to the sensor container 22 of the biomagnetic field detector 20, and fixed at a position of the nonmagnetic member 50 relative to the biomagnetic field detector 20. Further, a marker 51 which is radiation-nontransmissible and nonmagnetic is provided on a surface of the nonmagnetic member 50 opposite to the biomagnetic field detector 20.

The nonmagnetic member 50 is nonmagnetic. Being magnetic is not preferred because the magnetism may have a negative impact on detection results from the biomagnetic field detector 20. Further, the nonmagnetic member 50 is preferably radiation-nontransmissible in order to prevent projection into a radiological image. Examples of the material of the nonmagnetic member 50 include plastics, fiber reinforced plastics, and the like.

There is no particular limitation for the thickness of the nonmagnetic member 50. However, when the nonmagnetic member 50 is too thick, the distance between the subject S and the biomagnetic field detector 20 is large. This may attenuate the biomagnetic field of the subject S which is to be detected by the biomagnetic field detector 20. Therefore, the thickness of the nonmagnetic member 50 is preferably 4 mm or less, more preferably 2 mm or less.

There is no particular limitation for the marker 51 as long as it is radiation-nontransmissible and nonmagnetic. A radiation-transmissible marker 51 is not preferred in that the projection of the marker 51 cannot be produced in a radiological image, resulting in problems to elucidate the positional relationship among the radiation emitting unit 10, the biomagnetic field detector 20, and the radiation sensitive material 30. A magnetic marker 51 is not preferred in that it may have a negative impact on the detection precision of the biomagnetic field detector 20.

Examples of the material of the marker 51 include aluminum, titanium, brass, and the like.

There is no particular limitation for the shape of the marker 51, and examples thereof include circular, polygonal, and the like.

There is no particular limitation for the number of the marker 51 as long as it is more than one. The number of the marker 51 is preferably larger in order to increase the precision of determining the shape of a measurement target. The number of the marker 51 is preferably smaller in order to prevent overlapping of the radiological image of the markers 51 with the radiological image of an examination target of a subject in radiological images. Considering the both, the number of the marker 51 is preferably 2 or more and 6 or less, more preferably 2 or more and 4 or less.

There is no particular limitation for the position where the marker 51 is provided, but the marker 51 is preferably provided around the nonmagnetic member 50 in order to prevent overlapping of the radiological image of the marker 51 with the radiological image of the subject S.

A positioning mechanism (not shown) configured to specify the position of the radiation sensitive material 30 relative to the nonmagnetic member 50 may be provided in place of the radiation-nontransmissible and nonmagnetic marker 51 in FIG. 3 as an another example in which the precision of correlating detection results from the biomagnetic field detector 20 to morphological positions of an organ as the measurement target is increased. Specific examples of the positioning mechanism include a rail mechanism, and examples of the rail mechanism include a groove, a slit, and the like. The positioning mechanism may be provided so as to span the biomagnetic field detector 20 and the nonmagnetic members 50, and the radiation sensitive material 30 may be engaged with the rail mechanism. When the radiation sensitive material 30 is engaged with the rail mechanism and is pushed into the deepest area between the biomagnetic field detector 20 and the nonmagnetic member 50, the position of the radiation sensitive material 30 can be specified.

Moreover, a grid is widely used in order to remove scattered radiation when radiation is emitted. The grid is a nonmagnetic body made of lead foil and the like, and thus does not have a negative impact on detection results from the biomagnetic field detector 20. Therefore, the grid can be used without causing any significant problems in the present invention.

Returning to FIG. 1, there is no particular limitation for the arrangement of the radiation emitting unit 10, the biomagnetic field detector 20, and the radiation sensitive material 30 as long as the radiation sensitive material 30 is arranged between the examination region T where the examination target of the subject S is to be positioned and the biomagnetic field detector 20. However, it is preferred that the radiation emitting unit 10 in the present invention is configured to emit a radiation X towards the anterior side of the subject S from the posterior side of the subject S, and the radiation sensitive material 30 is provided in the anterior side of the subject S, and the biomagnetic field detector 21 of the biomagnetic field detector 20 is provided in the front side of the radiation sensitive material 30. This is because the biomagnetic field detector 20 may be projected when imaging the subject S with the radiation emitting unit 10, and a precise radiation image may be difficult to be obtained according to the conventional configuration, and because the magnetism from a cartridge in which the radiation sensitive material 30 is enclosed has a negative impact on detection results from the biomagnetic field detector 20. For example, a configuration can be mentioned in which the radiation emitting unit 10 is a chest X-ray emitting unit configured to emit X-rays towards the chest of the subject S from the posterior side of the subject S, and the biomagnetic field detector 21 is a cardiobiomagnetic field detector configured to detect cardiomagnetism arising from the heart of the subject S. This enables both the radiological images of the heart, chest, and the like of the subject S and the cardiomagnetism and others arising from the heart of the subject S to be obtained without moving the subject S.

Second Embodiment

Figure 4:
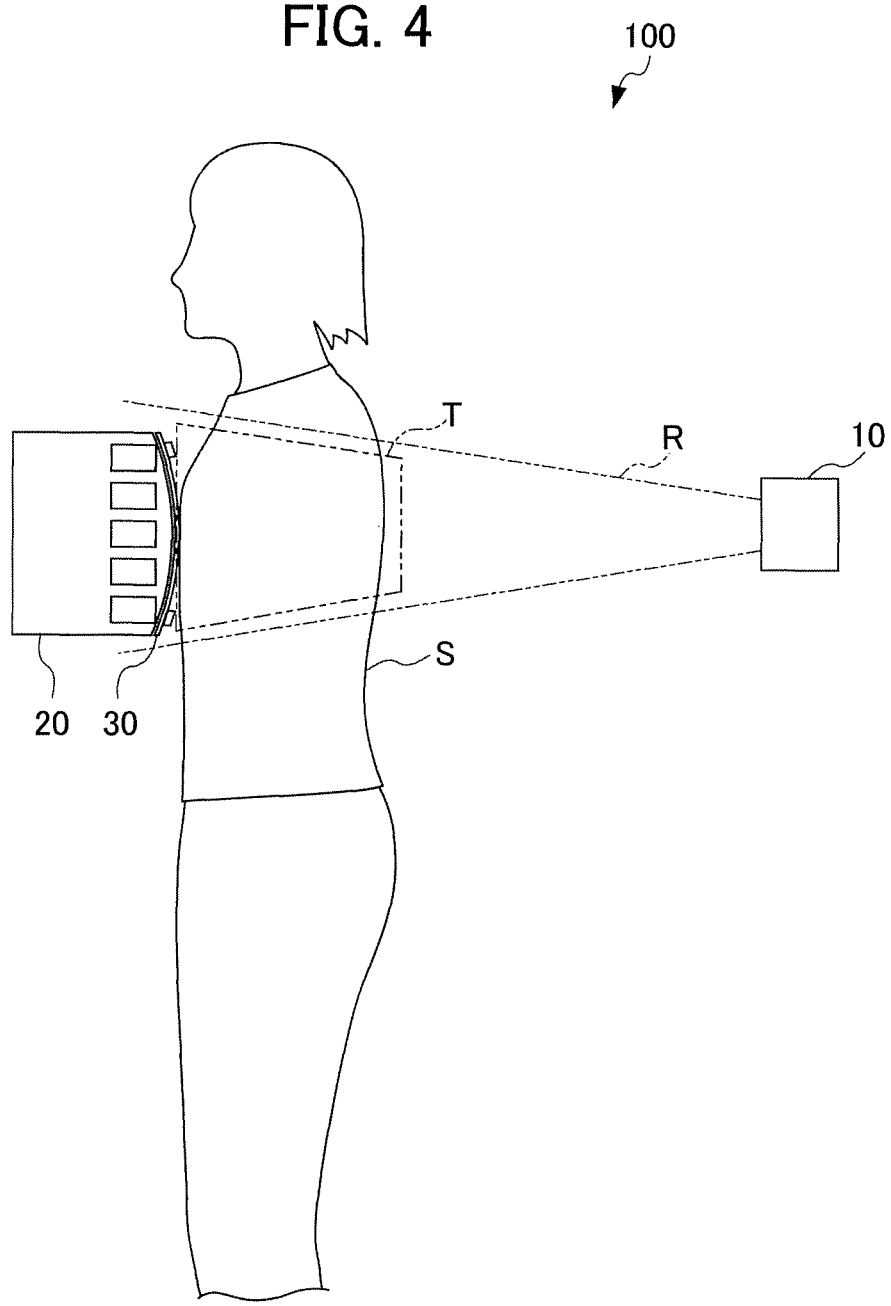
FIG. 4 shows a schematic view of a biological information measuring apparatus 100 according to a second embodiment of the present invention.

Next, the second embodiment of the present invention will be described. FIG. 4 shows a schematic view of a biological information measuring apparatus 100 according to the second embodiment of the present invention.

The subject S lies in the prone position (in the abdominal position) in the first embodiment while the subject S is in the standing position in the second embodiment. Others are the same as in the first embodiment.

Examinations according to the first embodiment in which the bed 40 is used are intended for in-hospital thorough examinations. On the other hand, the subject S may be in the standing position according to the second embodiment. Therefore, magnetocardiography can be performed at the same time as chest plain radiography which is generally performed in the standing position. Further this enables simple examinations in an examination car and the like.

An embodiment where the radiological images of the heart, chest, and the like and the cardiomagnetism of the subject S are obtained can be significantly effective in the case of mass screening. To date, a plurality of electrodes need to be directly attached to the skin of a subject in electrocardiography. This may impose emotional stress on female subjects, and require an examiner dedicated for electrocardiography to be assigned. In contrast, magnetocardiographic examinations can be performed while a subject wears a T-shirt and the like, and thus stress can be significantly reduced which may be imposed on female subjects. Further, acquisition of radiological images and magnetocardiographic examinations can be performed at the same place. Advantageously, this can save the labor of examiners.

It is noted that there is no particular limitation for the body position of the subject S, but it may be the prone position (abdominal position), the standing position as well as the seated position although they are not shown.

Third Embodiment

Figure 5:
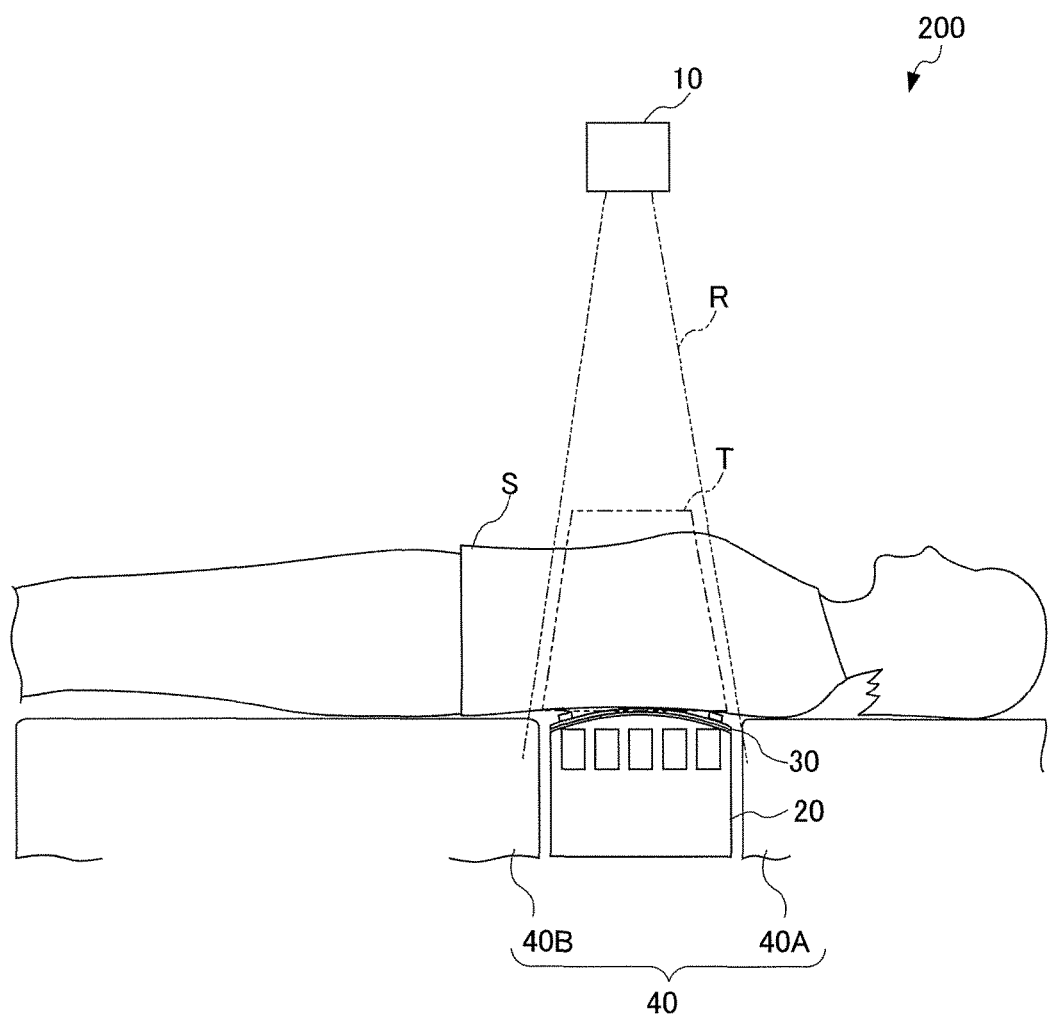
FIG. 5 shows a schematic view of a biological information measuring apparatus 200 according to a third embodiment of the present invention.

Next, the third embodiment of the present invention will be described. FIG. 5 shows a schematic view of a biological information measuring apparatus 200 according to the third embodiment of the present invention.

The subject S lies in the prone position (abdominal position), and the examination target of the subject S is the chest in the first embodiment. The third embodiment differs in that the subject S lies in the supine position (dorsal position), and the examination targets of the subject S are the spinal cord/spinal nerve, and the heart from the posterior side. Others are the same as in the first embodiment.

It is preferred that the radiation emitting unit 10 is configured to emit the radiation X towards the anterior side of the subject S from the posterior side of the subject S, and the radiation sensitive material 30 is provided in the anterior side of the subject S, and the biomagnetic field detector 21 of the biomagnetic field detector 20 is provided in the front side of the radiation sensitive material 30 as described above. Alternatively, it is also preferred that the radiation emitting unit 10 is configured to emit the radiation X towards the posterior side of the subject S from the anterior side of the subject S, and the radiation sensitive material 30 is provided in the posterior side of the subject S, and the biomagnetic field detector 21 of the biomagnetic field detector 20 is provided in the back side of the radiation sensitive material 30 as shown in FIG. 5. As a specific configuration, a configuration can be mentioned in which the radiation emitting unit 10 is a spinal-cord X-ray emitting unit configured to emit X-rays towards the spinal cord of the subject S from the anterior of the subject S, and the biomagnetic field detector 20 is a spinal biomagnetic field detector configured to detect spinal magnetism arising from the spinal cord of the subject S. This enables both the radiological images of the spinal cord, heart, and the like of the subject S and the spinal magnetism arising from the spinal cord/heart of the subject S to be obtained without moving the subject S.

Fourth Embodiment

Figure 6:
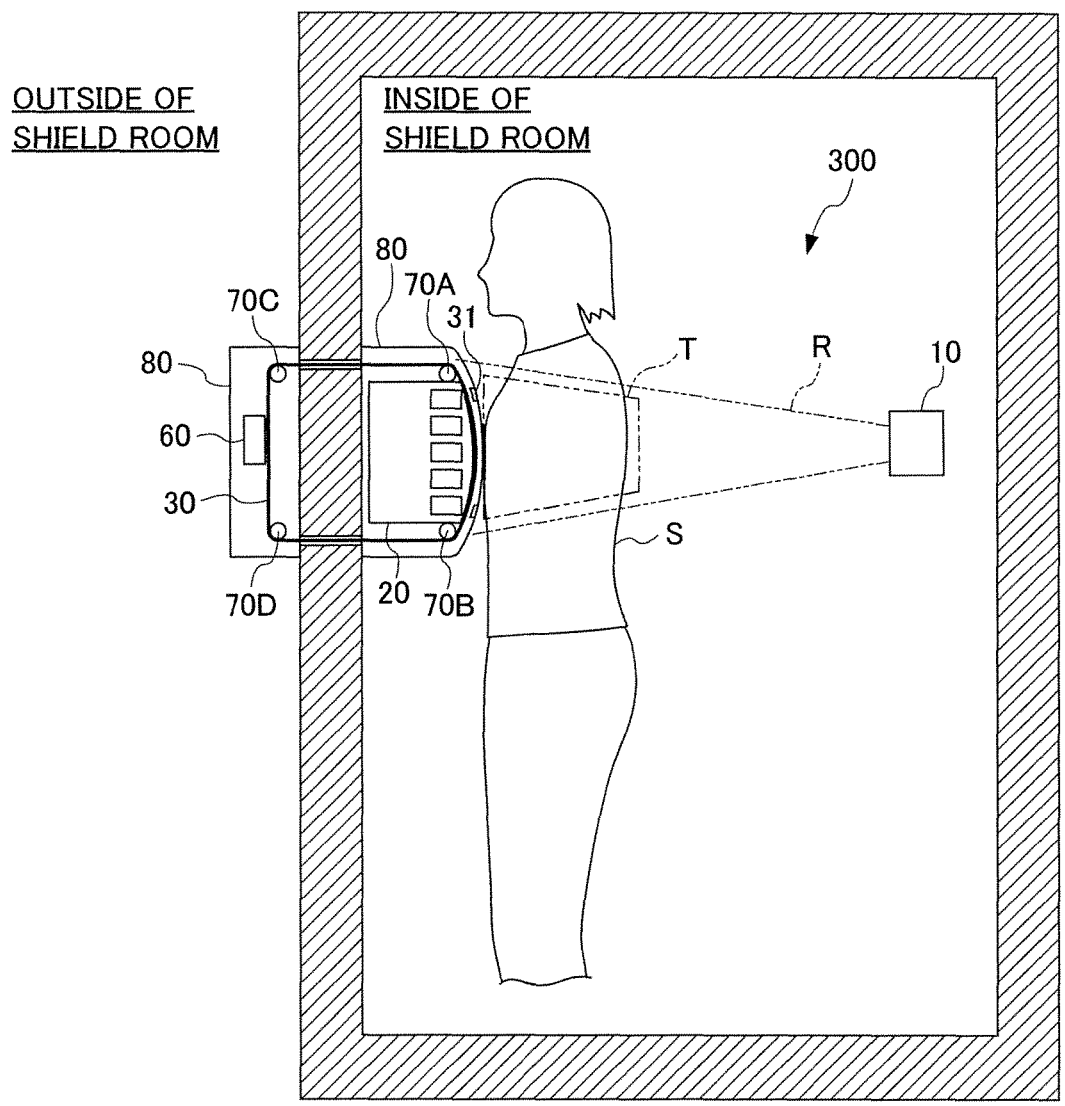
FIG. 6 shows a schematic view of a biological information measuring apparatus 300 according to a fourth embodiment of the present invention.

Next, the fourth embodiment of the present invention will be described. FIG. 6 shows a schematic view of a biological information measuring apparatus 300 according to the fourth embodiment of the present invention.

The radiation sensitive material 30 is of a single sheet-like form (sheet-like) or a plate-like form in the second embodiment. The fourth embodiment differs in that the radiation sensitive material 30 is cylindrical, and rollable along the peripheral portion of the biomagnetic field detector 20. Further, in the second embodiment, the radiation sensitive material 30 irradiated with the radiation R is first removed, and then the radiation sensitive material 30 is transferred to and placed in a radiological-image read-out device (not shown in FIG. 4) installed outside a magnetism and radiation-blocking room (shield room) where the biological information measuring apparatus 100 is placed. In contrast, the fourth embodiment differs in that the radiation sensitive material 30 irradiated with the radiation R is rolled so that the radiation sensitive material 30 is directed to the outside of a room (shield room) in which the biological information measuring apparatus 300 is placed, and then the radiation sensitive material 30 can be placed in the radiological-image read-out device 60 without removing the radiation sensitive material 30. In the fourth embodiment, parts indicated by the same reference numbers as in FIG. 4 are the same as those in the second embodiment.

Rollers 70 (70A, 70B, 70C, 70D) are provided at the peripheral portion of the biomagnetic field detector 20. The rollers 70 are provided at both the inside and outside of the room (shield room) in which the biological information measuring apparatus 300 is placed. Further, the radiation sensitive material 30 is rollably arranged along the rollers 70A to 70D.

The radiological-image read-out device 60 is arranged in the vicinity of a surface where a portion of the radiation sensitive material 30 outside the shield room is exposed so that the radiological-image read-out device 60 can read out information detected by the radiation sensitive material 30. Further, a light-blocking nonmagnetic cover 80 is provided outside the shield room so as to enclose the radiation sensitive material 30 and the radiological-image read-out device 60. Further, the cover 80 is also provided inside the shield room so as to enclose the radiation sensitive material 30, and the magnetic marker 31 (marker coil) is arranged on the inner surface of the cover 80 in such a way that rotation of the radiation sensitive material 30 is not interfered. It is noted that the magnetic marker 31 may be a nonmagnetic and radiation-nontransmissible maker having a known positional relationship with the biomagnetic field detector 20, and markers (the magnetic marker 31 and the like) may be arranged on either the inner surface or the outer surface of the cover 80.

The fourth embodiment is preferred in that information detected by the radiation sensitive material 30 can be read out without removing the radiation sensitive material 30 irradiated with the radiation R, and thus biological information can be measured without imposing excessive burden on examiners in charge even when a larger number of examinations are performed.

It is noted that the fourth embodiment is described with reference to a case where the subject S is in the standing position based on the second embodiment, but the fourth embodiment is not limited to this. Even when the subject S lies in the prone position (abdominal position) as in the first embodiment, or the subject S lies in the supine position (dorsal position) as in the third embodiment, a configuration similar to the fourth embodiment enables information detected by the radiation sensitive material 30 to be read out without removing the radiation sensitive material 30 irradiated with the radiation R.

Fifth Embodiment

Figure 7:
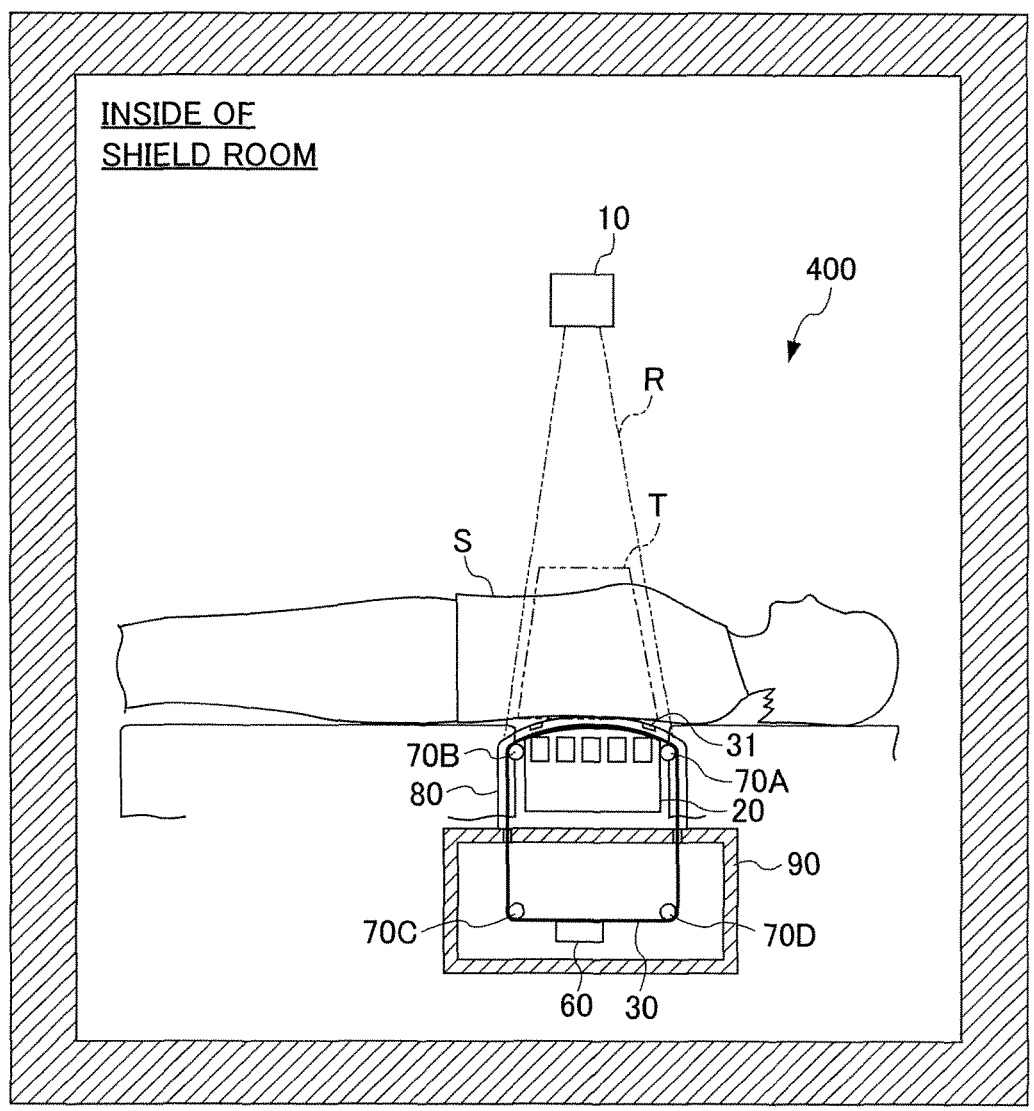
FIG. 7 shows a schematic view of a biological information measuring apparatus 400 according to a fifth embodiment of the present invention.

Next, the fifth embodiment of the present invention will be described. FIG. 7 shows a schematic view of a biological information measuring apparatus 400 according to the fifth embodiment of the present invention.

The fifth embodiment is the same as the fourth embodiment in that information detected by the radiation sensitive material 30 can be read out without removing the radiation sensitive material 30 irradiated with the radiation R. In the fourth embodiment, the radiological image read-out device 60 is provided outside the shield room. The fifth embodiment differs in that the radiological-image read-out devices 60 is provided inside the shield room. It is noted that the configuration shown in FIG. 7 is based on the third embodiment (FIG. 5), and parts indicated by the same reference numbers as in FIG. 5 are the same as those in the third embodiment.

The rollers 70 (70A, 70B, 70C, 70D) are provided at the peripheral portion of the biomagnetic field detector 20. The rollers 70 are provided inside a magnetism and radiation-blocking room (shield room) in which the biological information measuring apparatus 400 is provided. Further, the radiation sensitive material 30 is rollably arranged along the rollers 70A to 70D.

The radiological image read-out device 60 is arranged underneath the radiation sensitive material 30 so that information detected by the radiation sensitive material 30 can be read out. Further a magnetic shield 90 is provided below the biomagnetic field detector 20 so as to enclose the radiation sensitive material 30 and the radiological image read-out device 60. Further, the nonmagnetic cover 80 is provided above the magnetic shield 90 so as to enclose the radiation sensitive material 30, and the magnetic marker 31 (marker coil) is arranged on the inner surface of the covering 80 in such a way that rotation of the radiation sensitive material 30 is not interfered. It is noted that the magnetic marker 31 may be a nonmagnetic and radiation-nontransmissible maker having a known positional relationship with the biomagnetic field detector 20, and markers (the magnetic marker 31 and the like) may be arranged on either the inner surface or the outer surface of the cover 80.

The fifth embodiment is preferred in that information detected by the radiation sensitive material 30 can be read out without removing the radiation sensitive material 30 irradiated with the radiation R, and thus biological information can be measured without imposing excessive burden on examiners in charge even when a larger number of examinations are performed.

It is noted that the fifth embodiment is described with reference to a case where the subject S lies in the supine position (dorsal position) based on the third embodiment, but the fifth embodiment is not limited to this. Even when the subject S lies in the prone position (abdominal position) as in the first embodiment, or the subject S is in the standing position as in the second embodiment, a configuration similar to the fifth embodiment enables information detected by the radiation sensitive material 30 to be read out without removing the radiation sensitive material 30 irradiated with the radiation R.

EXAMPLES

Below, the present invention will be described specifically with reference to Examples, but the present invention shall not be limited to these.

<Test 1> Capturing of Radiological Image Under Biomagnetic Field Detecting Device in Operation A nonmagnetic imagining plate (FCR from FUJIFILM Corporation) is attached at a biomagnetic field detecting surface of an SQUID device (a biomagnetic field measuring apparatus developed in the joint research of Tokyo Medical and Dental University and Kanazawa Institute of Technology) with a magnetized cartridge removed. Then, the imagining plate is adjusted for the chest, cervical vertebrae, and lumbar vertebrae of a subject, and the chest, cervical vertebrae, and lumbar vertebrae were irradiated with X-rays under the SQUID device in operation using an X-ray emitting device (Product name: HF8015H from Mikasa X-Ray Co., Ltd.). Subsequently, the imaging plate was stored in a cartridge, and then placed in a radiological image read-out device to display an X-ray image on a display device. The X-ray images of the chest, cervical vertebrae, and lumbar vertebrae are shown in FIG. 8.

Figure 8A:
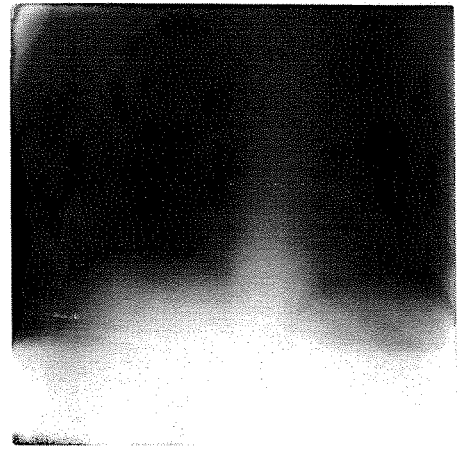
FIG. 8 shows X-ray images of the chest, cervical vertebrae, and lumbar vertebrae under a biomagnetic field detector in operation.
Figure 8B:
Figure 8C:
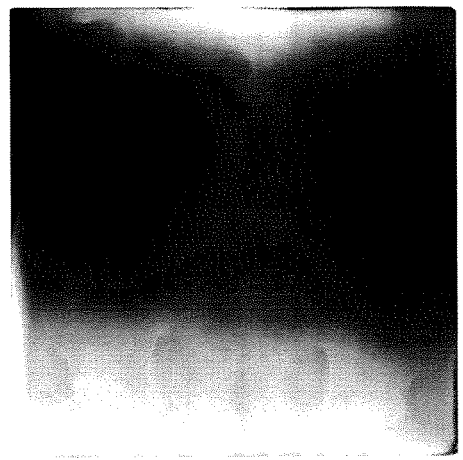

As demonstrated in FIG. 8, the chest, cervical vertebrae, and lumbar vertebrae of the subject were clearly imaged, and the biomagnetic field detecting surface were not projected into the X-ray images even when the SQUID device was in operation and in the middle of detecting biomagnetic field of the subject.

<Test 2> Studies of how Noise from Imaging Plate Affects Biomagnetic Field Detecting Device Test Example 2-1

Figure 9A:
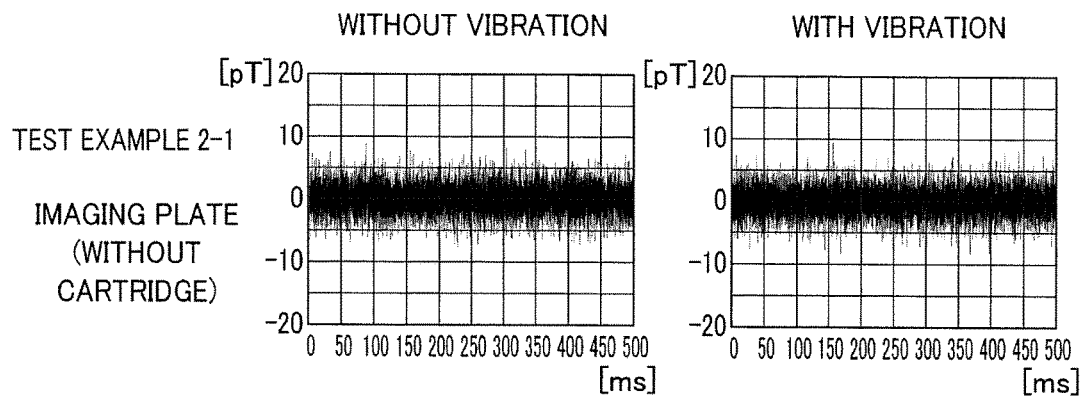
FIG. 9 shows the levels of noise from an imaging plate at the biomagnetic field detector.
Figure 9B:
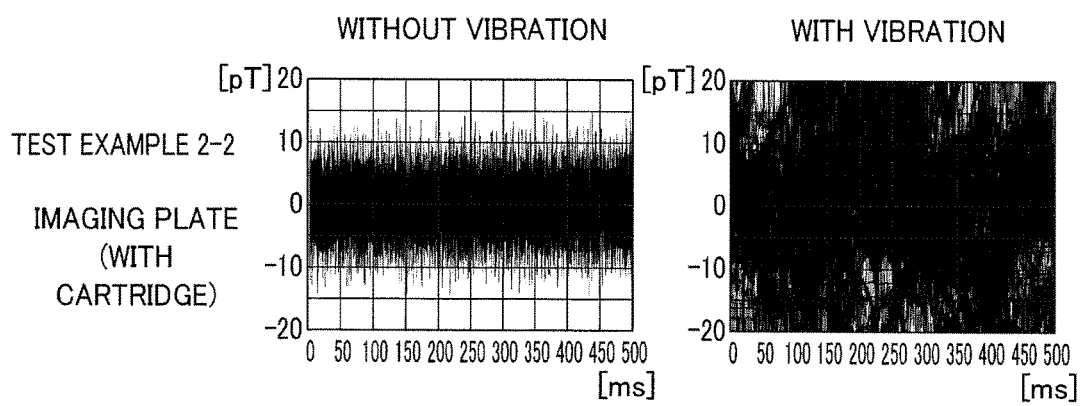
Figure 9C:
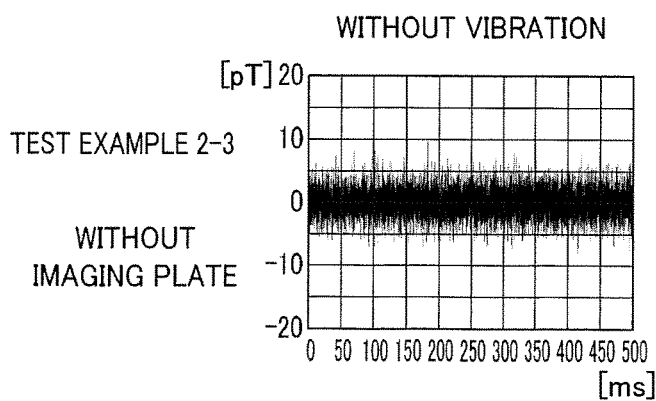

The imagining plate was attached to the biomagnetic field detecting surface (SQUID sensor) of the aforementioned SQUID device with a magnetized cartridge removed. Subsequently, noise detected by the biomagnetic field detecting surface was measured while the SQUID device was in operation for two cases: a case where vibration was not applied to the imagining plate and a case where vibration of about 3 cm and 1 Hz was applied. Results are shown in FIG. 9.

Test Example 2-2

Noise detected by the biomagnetic field detecting surface was measured in accordance with the same approach as in Test Example 2-1 except that the imaging plate was enclosed in a magnetized cartridge. Results are shown in FIG. 9.

Test Example 2-3

Noise detected by the biomagnetic field detecting surface was measured in accordance with the same approach as in Test Example 2-1 except the imaging plate was not attached to the biomagnetic field detecting surface of the SQUID apparatus. Results are shown in FIG. 9.

[Results]

In Test Example 2-1, the level of noise detected by the biomagnetic field detecting surface was low, and was not significantly different from that in Test Example 2-3. Results were similar for the case where vibration was applied to the imaging plate. These results suggest that the extent of negative impacts on the detection precision of the biomagnetic field detecting surface will be within the acceptable range because the imaging plate itself is nonmagnetic.

On the other hand, the level of noise detected by the biomagnetic field detecting surface was very large in Test Example 2-2, which means that the biomagnetic field of the subject was not detected at the biomagnetic field detecting surface in high precision. This is likely because the cartridge includes a magnetic material which has a negative impact on the biomagnetic field detecting device.

<Test 3> Magnetocardiogram Measurement with Imaging Plate Attached to Biomagnetic Field Detecting Surface The imagining plate was attached to the biomagnetic field detecting surface of the aforementioned SQUID device with a magnetized cartridge removed. Subsequently, the biomagnetic field detecting surface was directed to the chest of a subject, and then the SQUID device was turned on to perform magnetocardiogram measurements. Results are shown in FIG. 10.

Figure 10:
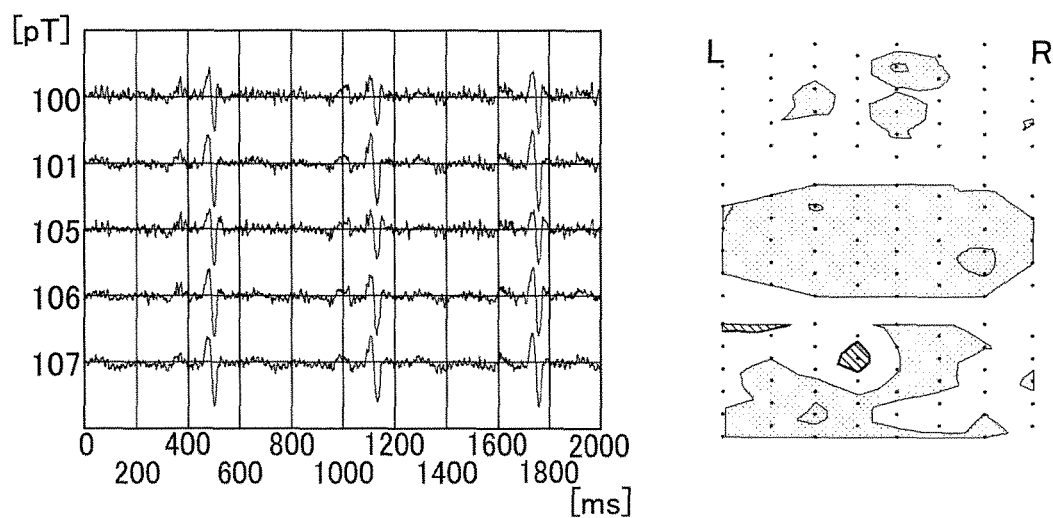
FIG. 10 shows magnetocardiograms when the imaging plate is arranged over the biomagnetic field detecting surface.

As demonstrated in FIG. 10, magnetocardiograms were able to be measured in sufficiently good precision even when the imaging plate was attached to the biomagnetic field detecting surface because the imagining plate itself was nonmagnetic.

EXPLANATION OF REFERENCE NUMERALS 1, 100, 200, 300, 400 Biological information measuring apparatus
10 Radiation emitting unit
20 Biomagnetic field detector
21 Magnetic sensor
22 Sensor container
30 Radiation sensitive material
31 Magnetic marker
40 Bed
50 Nonmagnetic member
51 Radiation-nontransmissible and nonmagnetic marker
60 Radiological-image read-out device
70 (70A, 70B, 70C, 70D) Roller
80 Cover
90 Magnetic shield
S Subject
R Radiation
T Examination region

The invention claimed is:

1. A biological information measuring apparatus, comprising:
    a radiation emitting unit configured to emit radiation to a subject;
    a biomagnetic field detector configured to detect a biomagnetic field of the subject; and
    a radiation sensitive material having sensitivity to the radiation, having enough size for enabling radiography of an examination target of the subject, and being nonmagnetic,
    the radiation sensitive material being arranged between an examination region where the examination target of the subject is to be positioned and the biomagnetic field detector.

2. The biological information measuring apparatus according to claim 1, wherein the biomagnetic field detector comprises:
    a magnetic sensor configured to detect the biomagnetic field of the subject; and
    a sensor container configured to contain the magnetic sensor,
    the sensor container having a biomagnetic field detecting surface, the biomagnetic field detecting surface facing the examination region where the examination target of the subject is to be positioned, and
    the radiation sensitive material being arranged over the biomagnetic field detecting surface.

3. The biological information measuring apparatus according to claim 2, wherein the radiation sensitive material is flexible.

4. The biological information measuring apparatus according to claim 2, wherein the radiation sensitive material is stored in a state where the radiation sensitive material is enclosed in a storage member, the storage member being nontransmissible of visible light and being nonmagnetic.

5. The biological information measuring apparatus according to claim 2, wherein a magnetic marker configured to generate a predetermined magnetic field is arranged on a surface side of the radiation sensitive material.

6. The biological information measuring apparatus according to claim 2, further comprising a nonmagnetic member covering the radiation sensitive material,
    a position of the nonmagnetic member relative to the biomagnetic field detector being fixed, and
    a radiation-nontransmissible and nonmagnetic marker being arranged on a surface of the nonmagnetic member opposite to a side of the biomagnetic field detector.

7. The biological information measuring apparatus according to claim 2, further comprising:
    a nonmagnetic member covering the radiation sensitive material and fixed at a position relative to the biomagnetic field detector; and
    a positioning mechanism configured to specify the position of the radiation sensitive material relative to the nonmagnetic member.

8. The biological information measuring apparatus according to claim 1, wherein the radiation sensitive material is flexible.

9. The biological information measuring apparatus according to claim 8, wherein the radiation sensitive material is stored in a state where the radiation sensitive material is enclosed in a storage member, the storage member being nontransmissible of visible light and being nonmagnetic.

10. The biological information measuring apparatus according to claim 8, wherein a magnetic marker configured to generate a predetermined magnetic field is arranged on a surface side of the radiation sensitive material.

11. The biological information measuring apparatus according to claim 8, further comprising a nonmagnetic member covering the radiation sensitive material,
    a position of the nonmagnetic member relative to the biomagnetic field detector being fixed, and
    a radiation-nontransmissible and nonmagnetic marker being arranged on a surface of the nonmagnetic member opposite to a side of the biomagnetic field detector.

12. The biological information measuring apparatus according to claim 8, further comprising:
    a nonmagnetic member covering the radiation sensitive material and fixed at a position relative to the biomagnetic field detector; and
    a positioning mechanism configured to specify the position of the radiation sensitive material relative to the nonmagnetic member.

13. The biological information measuring apparatus according to claim 1, wherein the radiation sensitive material is stored in a state where the radiation sensitive material is enclosed in a storage member, the storage member being nontransmissible of visible light and being nonmagnetic.

14. The biological information measuring apparatus according to claim 13, wherein a magnetic marker configured to generate a predetermined magnetic field is arranged on a surface side of the radiation sensitive material.

15. The biological information measuring apparatus according to claim 13, further comprising a nonmagnetic member covering the radiation sensitive material,
    a position of the nonmagnetic member relative to the biomagnetic field detector being fixed, and
    a radiation-nontransmissible and nonmagnetic marker being arranged on a surface of the nonmagnetic member opposite to a side of the biomagnetic field detector.

16. The biological information measuring apparatus according to claim 13, further comprising:
    a nonmagnetic member covering the radiation sensitive material and fixed at a position relative to the biomagnetic field detector; and
    a positioning mechanism configured to specify the position of the radiation sensitive material relative to the nonmagnetic member.

17. The biological information measuring apparatus according to claim 1, wherein a magnetic marker configured to generate a predetermined magnetic field is arranged on a surface side of the radiation sensitive material.

18. The biological information measuring apparatus according to claim 1, further comprising a nonmagnetic member covering the radiation sensitive material;
    a position of the nonmagnetic member relative to the biomagnetic field detector being fixed, and
    a radiation-nontransmissible and nonmagnetic marker being arranged on a surface of the nonmagnetic member opposite to a side of the biomagnetic field detector.

19. The biological information measuring apparatus according to claim 1, further comprising:
    a nonmagnetic member covering the radiation sensitive material and fixed at a position relative to the biomagnetic field detector; and
    a positioning mechanism configured to specify the position of the radiation sensitive material relative to the nonmagnetic member.

* * * * *